United States Patent [19]

Scheid et al.

[11] Patent Number: 4,998,270
[45] Date of Patent: Mar. 5, 1991

[54] MAMMOGRAPHIC APPARATUS WITH COLLIMATED CONTROLLABLE X-RAY INTENSITY AND PLURALITY FILTERS

[75] Inventors: Carl C. Scheid, Delafield; James A. McFaul, Waukesha, both of Wis.

[73] Assignee: General Electric Company, Milwaukee, Wis.

[21] Appl. No.: 403,762

[22] Filed: Sep. 6, 1989

[51] Int. Cl.⁵ .......................... A61B 6/04; G21K 1/00
[52] U.S. Cl. .................................... 378/155; 378/145; 378/37
[58] Field of Search ............... 378/108, 109, 112, 145, 378/37

[56] References Cited

U.S. PATENT DOCUMENTS

| | | | |
|---|---|---|---|
| 4,020,347 | 4/1977 | Geluk | 378/37 |
| 4,051,377 | 9/1977 | Kemner et al. | 378/108 |
| 4,096,391 | 6/1978 | Barnes | 378/155 |
| 4,122,350 | 10/1978 | Lipthay et al. | 378/37 |
| 4,203,037 | 5/1980 | Gur et al. | 378/37 |
| 4,744,099 | 5/1988 | Huettenrauch et al. | 378/37 |
| 4,763,343 | 8/1988 | Yanaki | 378/112 |

Primary Examiner—Edward P. Westin
Assistant Examiner—Kim-Kwok Chu
Attorney, Agent, or Firm—James H. Beusse; James O. Skarsten

[57] ABSTRACT

A method and apparatus for improving imaging in an X-ray mammography machine having a controllable X-ray source incorporates apparatus for directing the X-ray beam in a preselected configuration onto at least a portion of a target area. The creation intensity of the beam is detected in each of a plurality of substantially equal segments of the target area and a first segment of lowest radiation intensity is identified. The X-ray source is adjusted to establish a predetermined radiation intensity in the identified first segment. Second segments are then identified each having a radiation intensity greater than a predetermined percentage of the radiation intensity in the identified first segment. The radiation intensity directed toward the identified second segments is then automatically attenuated by a control system responsive to the radiation intensity detected in the second segments. The attenuation is achieved by moving collimators into the beam so as to reduce the radiation directed towards the second segments. The beam is scanned over the target and continuously adjusted in accordance with the radiation detected in each of the segments of the beam. In this manner, each area of the target receives just sufficient radiation to provide proper imaging without overexposing area of the target which have less attenuation than other areas.

20 Claims, 10 Drawing Sheets

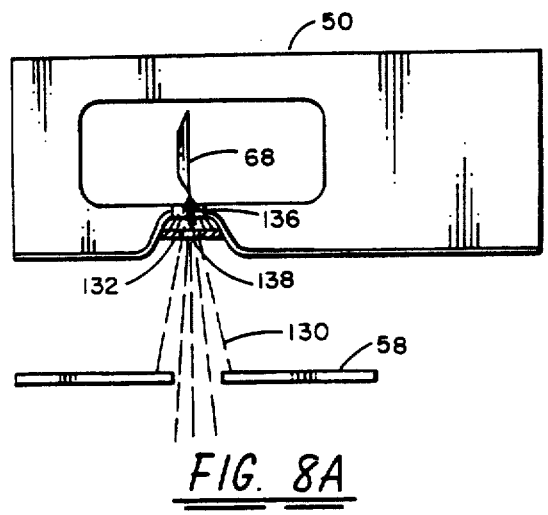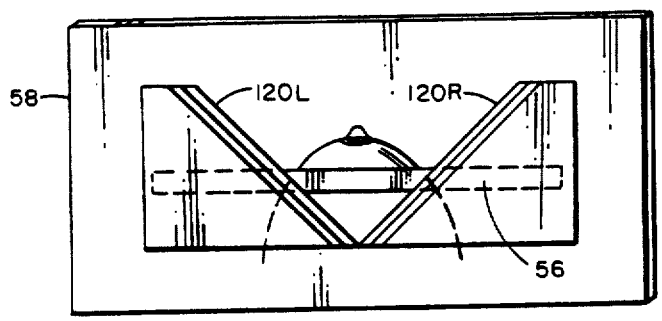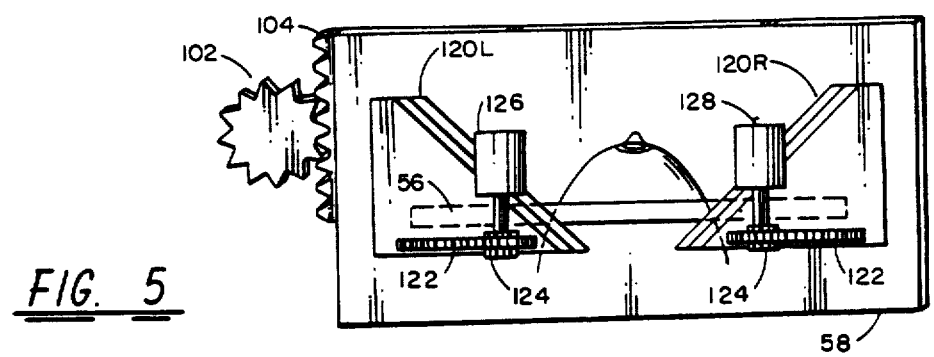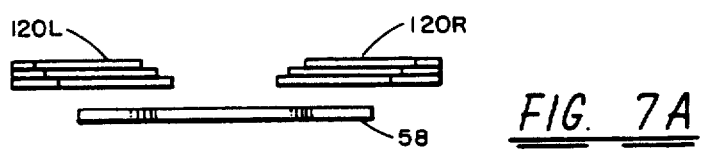

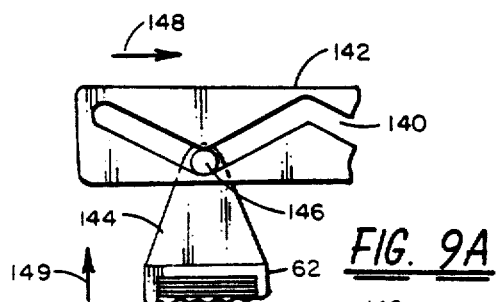
FIG. 9A
FIG. 9B
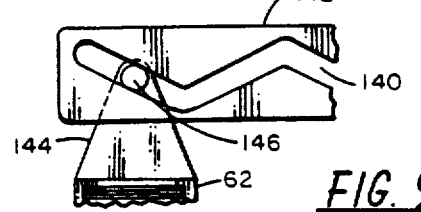
FIG. 9C
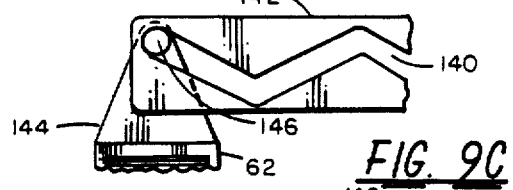
FIG. 9D
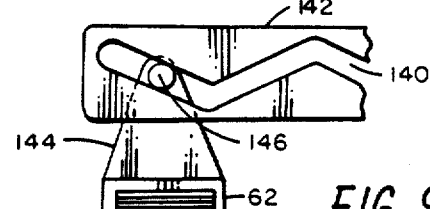
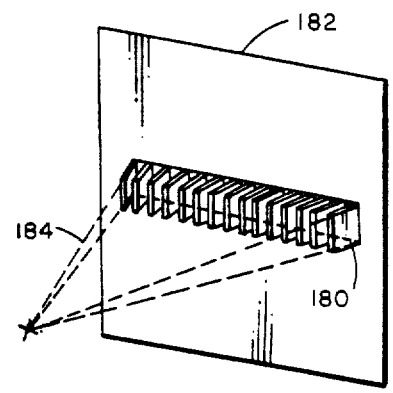
FIG. 11A
FIG. 11B
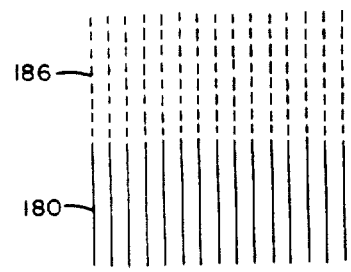
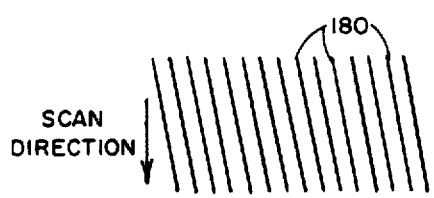
FIG. 11C
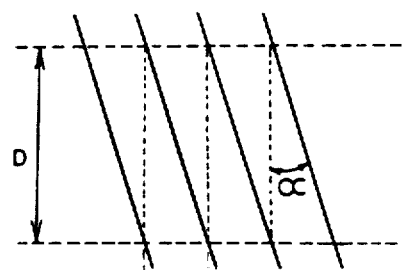
FIG. 11D

MAMMOGRAPHIC APPARATUS WITH COLLIMATED CONTROLLABLE X-RAY INTENSITY AND PLURALITY FILTERS

The present invention relates to medical X-ray systems and, more particularly, to an improved method and apparatus for X-ray mammography. This application is related to co-pending applications Ser. No. (07/407,736) and Ser. No. (07/403,680).

BACKGROUND OF THE INVENTION

Mammography machines are used for X-ray examination of the female human breast to detect cancer or other growths. An exemplary version of such a machine is shown in FIG. 1. In general, the machine includes an operator control unit and X-ray generator portion indicated at 20. The portion 20 incorporates the control electronics for the machine as well as the power supply for an X-ray source. THe machine portion indicated at 22 is sometimes referred to as a C-arm assembly and includes a film table 24, an overlaying compression paddle 26 and an X-ray source 28. The C-arm assembly may be rotatable about a horizontal axis 30 for obtaining different angular images. A radiation shield 32 isolates the operator control area adjacent portion 30 from the patient area adjacent film table 24. The C-arm 22 is vertically adjustable, in the position shown in FIG. 1, to accommodate patients of different heights. The table 24 accepts standard X-ray film cassettes for image recording.

In conducting a mammography examination, a patient's breast is placed upon film table 24 and is compressed by compression paddle 26. The compression is required in order to have a substantially uniform density or thickness of the breast typically necessary to provide rather uniform X-ray image density characteristics. In other words, the conventional fixed X-ray exposure techniques generally yield sufficient image quality, i.e., contrast, if the breast has uniform thickness. Such compression procedures are often painful for the patient.

In addition, prior art mammography requires a manual selection of a single kVp and filter for each examination. At best, this may provide proper exposure, contrast and dose for only one portion of the target.

Another disadvantage is that prior art mammography requires manual adjustment of lead collimator blades, which manual adjustment creates two problems. One problem arises if the blades are too close to the skin line, in which case the background image exposure will not be suitable for good viewing. Another problem arises if the blades are left wide open, as is often the case, in which event the intense radiation will produce image fogging scatter.

Still another disadvantage is that prior art mammography involves manual placement of a single X-ray exposure detector. An error in placement of this single detector will produce an incorrect exposure.

Yet another disadvantage is that prior art mammography is subject to film reciprocity which results in increased patient dose if the selected technique factors produce a long exposure time.

A further disadvantage is that prior art mammography involves the use of metal or plastic interspaced grids. Such grids require higher energy X-ray radiation which results in increased patient dose and limited scatter rejection.

In addition to the discomfort associated with prior art mammography examinations attributable to forceful compression, a further disadvantage is a relatively high X-ray dosage necessary to provide sufficient contrast. The X-ray intensity may be set by a sensor located at the film table. The sensor responds to impinging X-rays to adjust the X-ray exposure time so as to set a desired exposure at the sensor location. Such sensor is generally set adjacent a patient's chest wall since that area represents the thickest breast area. Since the level of X-ray intensity for sufficient image contrast adjacent the chest wall is usually much higher than necessary in other areas, the image quality deteriorates toward the nipple due to overexposure of the film.

It is an object of the present invention to provide a mammography machine which overcomes the above as well as other disadvantages of the prior art.

SUMMARY OF THE INVENTION

The present invention includes a method and apparatus for obtaining a mammography X-ray image using a scan equalized procedure. An X-ray mammography machine is provided having a controllable X-ray source for generating an X-ray beam of selected radiation intensity. The X-ray source is mounted so as to be pivotable or tiltable about a preselected axis passing through the point source of radiation within the X-ray tube. The generated X-ray beam is collimated into a fan-shaped configuration which can be scanned over a target by pivoting of the X-ray source. Detection means is provided below the target area for sensing the intensity of radiation at the detector in each of a plurality of substantially equal segments of the target area. Signals representative of the intensity of radiation impinging on each of the target segments are provided and the lowest intensity segment is utilized as a control segment. The signal representative of radiation intensity reaching the control segment is utilized to control the kVp and Ma of the X-ray source to adjust the intensity at the control segment to a level sufficient to provide the desired image contrast. The output signals from the detector are continuously monitored during the scanning process and the X-ray source power adjusted to maintain the image contrast and exposure at the desired level throughout the full image scan.

The invention further provides for automatic collimation of the X-ray beam and to this end includes apparatus for attenuating the radiation outside a target being radiated. The attenuating means is also controlled by the signals received by the detector. In one form, the detector signals are monitored to identify segments receiving radiation intensity which is greater than a predetermined factor of the radiation intensity in the control segment. If a segment has a radiation intensity greater than the determined value, movable collimators are positioned so as to attenuate the radiation directed towards those segments. This procedure allows for improved skin line viewing of a target by reducing the exposure of an X-ray film in those areas outside the target. The collimators also provide the best image density outside the target so as to minimize film illuminator glare.

In conjunction with scanning of the X-ray beam, there is provided a fore collimator whose movement is synchronized with scanning of the beam so as to maintain the collimator in the X-ray beam path. An aft collimator positioned below the target is also moved in synchronism with scanning of the X-ray beam. The aft collimator is positioned over an X-ray film cassette and includes an X-ray impervious belt attached to each side of the collimator to block scatter radiation so that film exposure is only attributable to on-axis radiation passing through the target. In a preferred form, the aft collimator comprises a rectangular grid having a plurality of air interspersed grid elements which serve to further assist in inhibiting scatter radiation. The aft collimator is reciprocally moved transverse to the direction of scanning of the X-ray beam in order to eliminate grid lines caused by the air interspersed grid elements.

The invention further includes automatic selection of the best kVp and filter for the particular patient being examined. This includes apparatus for continuous automatic selection of kVp and filtration for establishing a preselected image contrast over all areas of the target. In addition to continuously adjusting the kVp and Ma for the X-ray source, the system further establishes a desired filter for maximizing contrast while minimizing patient X-ray dosage. The filter selection is based upon a prior knowledge and is chosen as a function of the selected kVp. The system automatically inserts the selected filter into the X-ray beam.

The invention further provides a method and apparatus for automatically and continuously controlling patient dose, image contrast and image exposure to a desired value for a particular imaging detector. System features include:

1. Scanning X-ray fan beam.
2. Multiple parallel detector oriented in the scan direction.
3. Means for continuously selecting the minimum exposure value.
4. Means for automatically and continuously varying kVp and Ma to provide the desired exposure and contrast.
5. Means for automatically varying the X-ray filter to maximize contrast and minimize patient dose.

BRIEF DESCRIPTION OF THE DRAWINGS

For a better understanding of the present invention, reference may be had to the following detailed description taken in conjunction with the accompanying drawings in which:

FIGS. 5 and 6 are more detailed plan views of the attenuator plates and fan beam collimator of FIG. 3;

FIGS. 7A-7D illustrate, in various views, the attenuator plates of FIG. 6;

FIGS. 8A and 8B illustrate a collimator for minimizing off-focus radiation from an X-ray source;

FIGS. 9A-9D illustrate one method of implementing reciprocating or Bucky motion of a scanning grid;

FIGS. 11A-11D illustrate arrangements of septa in a grid for eliminating grid lines without Bucky motion;

DETAILED DESCRIPTION OF THE PREFERRED EMBODIMENT

Figure 1:
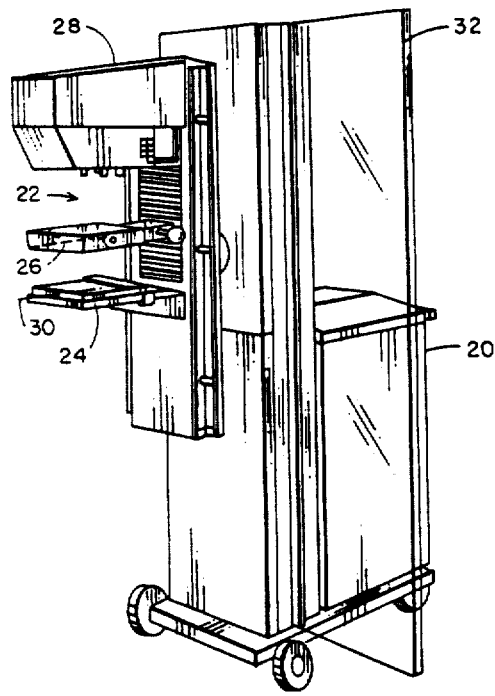
FIG. 1 is a perspective view of a prior art mammography machine.
Figure 2:
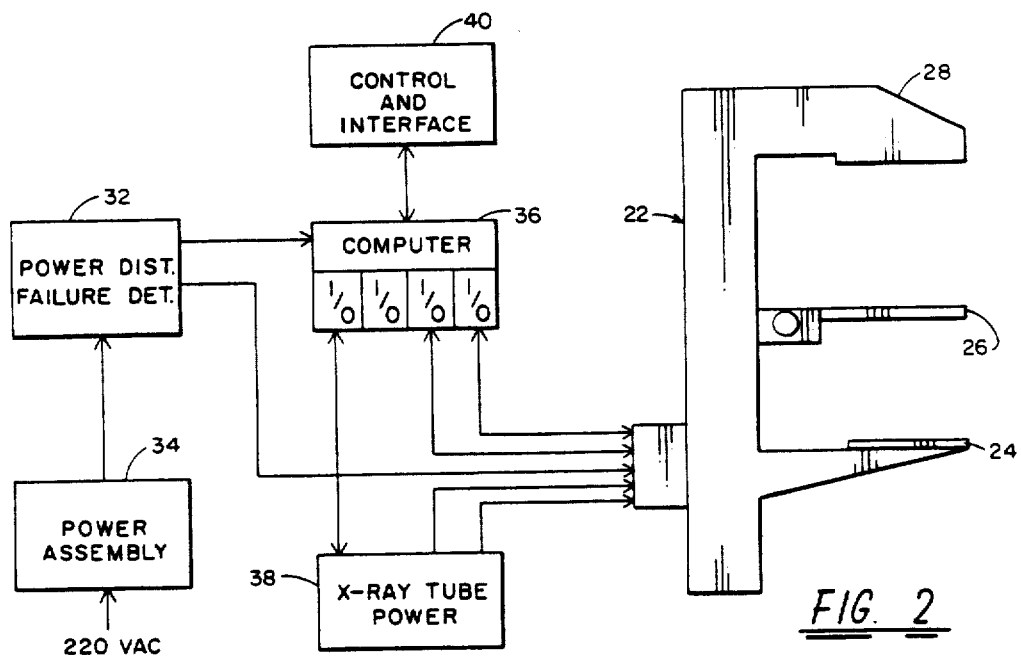
FIG. 2 is a simplified functional schematic representation of the machine of FIG. 1.

While FIG. 1 is a perspective view of a prior art mammography machine, FIG. 2 is a schematic representation of the various functional components of such a machine. These components are briefly described since, at this level of discussion, they are common to all electronically controlled mammography machines. The mammography machine, except for the X-ray tube, generally operates on low voltage power, e.g., 24volts direct current (VDC), supplied from a power distribution and power failure detection assembly 32. The assembly 32 receives power from power assembly 34. Power assembly 34 is in turn connected to a 220 volts alternating current (VAC) or other suitable power source and includes appropriate transformers, rectifiers and regulation circuits for generating the required direct current voltages for the machine.

Machine operation is under the control of a host processor (microcomputer), such as an 80C31, indicated at 36. Processor 36 provides an interface with a Varian generator 38 and with the X-ray sensors and C-arm drives in C-arm assembly 22. Processor 36 also provides closed loop control of the X-ray source inclusive of filament control and responding to X-ray sensors. The Varian generator 38 provides the high voltage for the X-ray source. Generally operation of the mammography machine is directed through a display controller and operator interface 40 which communicates with the processor 36.

In the operation of the mammography machine of the prior art, the operator sets a preselected kVp (X-ray tube anode voltage), a preselected Ma (X-ray tube current) and a back-up exposure time. As the exposure begins, the X-ray intensity is sensed at the film table 24. The sensor signal is integrated and the X-ray exposure terminated when the integrated value reaches a predetermined value for the particular film being used. Exposure is thus controlled only in the area of the sensor. As a result, thinner or less dense areas of the breast result in poor quality imaging. Thus, the relatively painful compression must be used by clamping the breast between film table 24 and compression paddle 26.

The present invention overcomes many of the disadvantages of the prior art mammography systems by implementation of a plurality of novel features. While each feature provides a significant improvement to prior art systems, the combination of features sets forth a substantially new system and method for obtaining mammography images. The major individual features can be identified as follows:

1. Conversion of the source of X-rays to substantially a "point" source and elimination of off-focus radiation.

2. Imaging using a scanning X-ray beam having a relatively thin cross-section in the scanning direction to reduce scatter radiation from the patient being examined.

3. Automatic collimation plates which confine the X-ray beam to the target area to allow viewing at the skin line along the target edge by reducing intensity at the edge.

4. An air interspersed grid positioned between the target area and an X-ray film for improving primary X-ray transmission to reduce patient X-ray dosage.

5. Reciprocating movement of the air interspersed grid with X-ray exposure interruption at each extreme of grid travel to eliminate grid lines.

6. An X-ray impervious belt moving concurrently with a scanning grid to block scattered X-ray radiation outside the grid area.

7. A multi-element X-ray detector positioned below the film table for detecting X-ray intensity in each of a plurality of small areas. The X-ray detectors are connected to a control system for continuous regulation of X-ray intensity during scanning so as to eliminate the requirement of breast compression.

8. Angularly varying the X-ray tube position during scanning to maintain X-ray focal direction at the scanning grid for decreasing exposure time and for improving tube loading.

9. Variable filter to provide optimum X-ray filtration for patient thickness.

Each of the above major features provides an improvement to existing mammography systems while the combination provides a new method and apparatus for mammography. These features as well as others will be separately described hereinafter.

A. SCANNING SYSTEM

Figure 3:
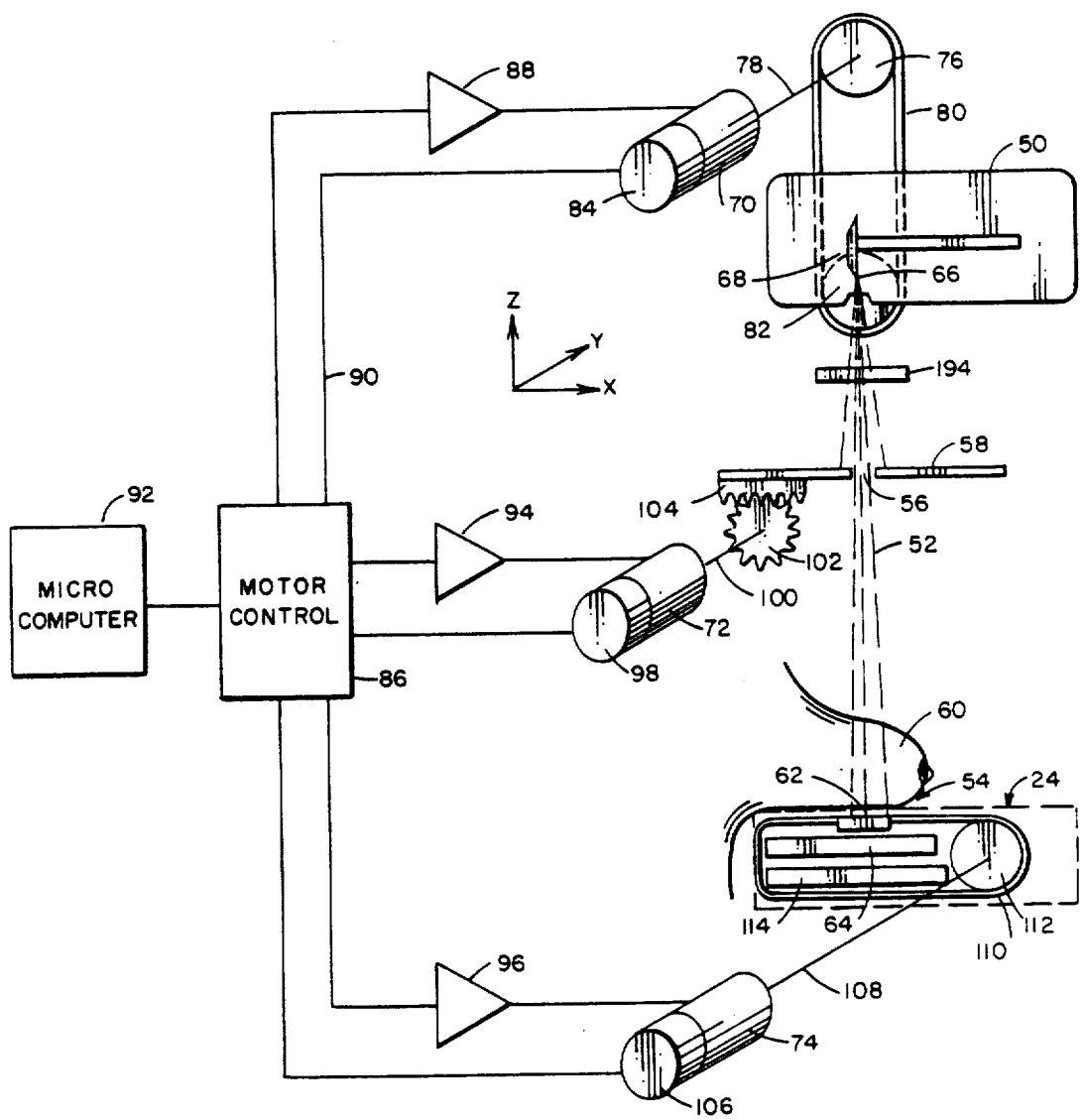
FIG. 3 is a schematic representation of one form of mammography system in accordance with the teaching of the present invention.

From a patient's perspective, the more significant advantage of the scan equalized mammography system of the present invention is the ability to provide an X-ray image without painful breast compression. From a physician's perspective, the advantages lie in improved image quality and reduced X-ray dose. These advantages are achieved, at least in part, by scanning of the X-ray beam so that only a portion of the target area is imaged at any time. Referring to FIG. 3, there is shown schematically a diagram of one embodiment of the present scanning system. An X-ray tube 50 is positioned above a film table 24 such that an X-ray beam 52 is directed toward a target area 54 on table 24. The beam 52 is collimated into a narrow fan-shaped beam in the X-axis direction. Collimation is accomplished primarily through a fore slot 56 in a fore collimator 58. After passage through the slit 56, the beam is directed through a target 60 and impinges on an aft slot or grid 62. The grid 62 reduces the acceptance of scattered radiation onto a film cassette 64 positioned beneath the target 60 in the film table 24. Since it is desirable to obtain an image of the entire target 60, it is necessary to scan the fan beam 52 over the entire area of the target 60. This scanning function requires a number of concurrent movements of elements in the system.

The initial motion of the beam is achieved by tilting or pivoting the X-ray tube 50 about a focal spot 66 on a rotating anode 68. Concurrently with pivoting of the X-ray tube 50, the fore collimator 58 must be moved such that the primary focal direction of the X-ray beam 52 is aligned with the slit 56. At the same time, the grid 62 must also be moved so as to be aligned with the beam 52. In the illustrative embodiment, each of the motions of the tube 50, the collimator 58 and the grid 62 are controlled by direct current (DC) motors 70, 72 and 74, respectively. Pivoting of tube 50 may be controlled by a belt and gear arrangement in which a driven gear 76 connected to a shaft 78 of motor 70 is rotated to drive a belt 80 which passes over a slave gear 82 fixed to the X-ray tube 50. An encoder 84 provides instantaneous feedback information as to the exact position of the gear 76 and therefore the pivot angle of the tube 50. The motor 70 and the encoder 84 are both coupled to a motor controller 86 which provides power to the motor 70 through a power amplifier 88 and receives the encoded position information from encoder 84 via line 90. The motor controller 86 is under control of a microprocessor based time/speed control system 92 which provides output signals to the motor controller to direct the scanning motion of the beam 52.

The microprocessor based speed controller 92 provides the signals to the motor controller 86 to drive each of the motors 70, 72 and 74 at corresponding speeds so as to coordinate the movement of the X-ray tube 50 with the movement of the fore collimator 58 and grid 62. The controller 86 provides signals through power amplifier 94 to the motor 72 and through power amplifier 96 to the motor 74. An encoder 98 is coupled to motor 72 and provides feedback signals to the motor controller 86 indicative of the position of the shaft 100 of motor 72. The motor shaft 100 is connected into a rack and pinion drive arrangement in which a pinion gear 102 mates with a rack gear 104 fixed to fore collimator 58. Rotation of gear 102 serves to drive the collimator 58 in a horizontal plane along the direction of the indicated X-axis.

The motor 74 also includes an encoder 106 which provides feedback information to motor controller 86 indicative of the angular position of motor shaft 108. In the illustrative embodiment, the grid 62 is connected to a drive belt 110 which is driven by a roller 112 connected to motor shaft 108. Driven rotation of the roller 112 moves the belt 110 to effect horizontal movement in the X-direction. The encoder 106 provides feedback signals to motor controller 86 indicative of the position of the grid 62. The motor controller 86 simultaneously performs closed loop control of each of the motors 70, 72 and 74 to assure concurrent driving of the tube 50, the fore collimator 58 and the grid 62. In this manner, the scanning motion of the X-ray beam 52 over the area of target 60 is achieved. The synchronization of the tube, fore slit, and grid does not have to be precise since the fore slit can be adjusted to create a fan beam slightly narrower than the grid.

Figure 4:
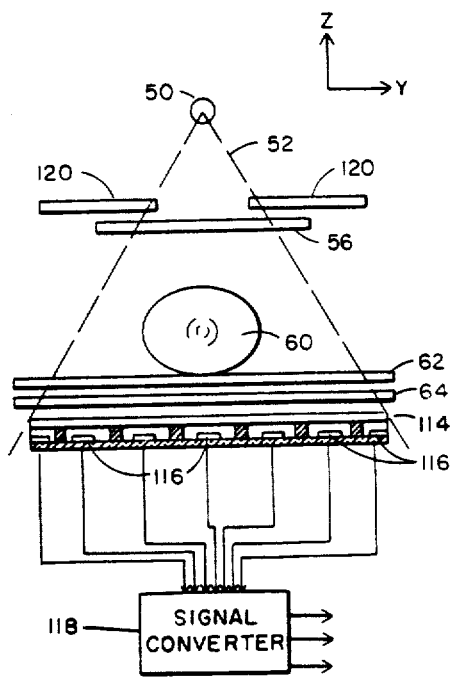
FIG. 4 is a simplified illustration of a portion of the system of FIG. 3 illustrating a multi-element X-ray detector.

It will be noted in FIG. 3 that there is indicated an X-ray intensity sensor or detector 114 positioned beneath the film cassette 64 in the film table 24. The X-ray detector 114 provides signals indicative of the intensity of the X-ray radiation reaching the detector through the target area. For a fan beam width of approximately one inch, the X-ray detector is effective to adjust the intensity of the beam in substantially one inch increments. While this arrangement provides a significant improvement over prior art systems, it is further desirable to divide each of the one inch width increments into a plurality of individual channels so as to eliminate the need for exact positioning of the target over the detector. For example, for a single detector extending the length of the scan direction, the target 60 must be positioned such that the region of maximum attenuation along the X-ray fan beam scan direction is always over the X-ray detector, i.e., the thickest part of a breast must be centered over the detector. By replacing the single detector by a plurality of parallel detectors, the exact positioning or centering of the target by the operator can be eliminated. Referring to FIG. 4, the single X-ray detector of the prior art is replaced by an array of strip detectors 116 each of which is connected to a controller 118 which converts the intensity of X-rays impinging on each of the detectors in the array 116 to corresponding electrical control signals. The number of elements in the array 116 may be varied depending upon the application. The array may be individual detector elements or they can be part of a linear ionization chamber or other suitable X-ray detection apparatus. In the preferred embodiment, a twelve element strip detector has been found suitable for use with a twelve inch wide film cassette. Each of the elements in the array then represents a one inch by one inch area of the target when scanned by a collimated one-inch thick X-ray beam. Within the target area, the controller 118 provides output signals to control the kVp of the X-ray tube and collimator blades. The tube kVp establishes an Ma for the tube based on preselected relationships between kVp and Ma. The one-inch by one-inch area is believed desirable since any smaller area might result in missing larger cysts or other abnormalities in the target area. For each scan beam across the area, i.e., perpendicular to the direction of beam scanning, twelve readings of intensity are provided by a twelve element detector. The controller 118 selects the lowest reading of the twelve readings as corresponding to the densest target area and uses that reading to control the kVp of the X-ray tube 50. Accordingly, the twelve element system sets the intensity of the X-ray energy to provide suitable contrast for the densest target area. Since the intensity level or kVp exposure is adjusted to give a uniform film density over a scan, it is no longer necessary to compress the target to a uniform density. A detailed description of a multi-element detector suitable for the present application is given in U.S. patent application Ser. No. 261,988, filed June 5, 1989, and assigned to General Electric Company, the disclosure of which is hereby incorporated by reference.

In addition to the improvement to be obtained by scanning of the X-ray beam and continuous adjustment of the X-ray intensity during scanning, the present invention also improves viewing of skin lines along a target area by reducing the intensity at the scan edge. This latter improvement is provided by movable slide plates which act as automatic collimators to track the skin line of a target during scanning. The automatic collimators are preferably tapered aluminum collimator blades indicated at 120 in FIG. 4 and are shown in more detail in FIGS. 5 and 6. The collimators 120 comprise independently controllable left and right triangular shaped attenuators 120L and 120R each driven by a corresponding rack 122 and pinion gear 124 arrangement from a respective DC electric motor 126, 128. The side collimator plates 120 or attenuators essentially taper the beam intensity to the target area at the skin line. Control of these plates is achieved through the controller 118 (FIG. 4). As each of the detector elements in the array 116 is sampled, the lowest detector signal is used to control the X-ray intensity. The remaining signals are each compared to the lowest one and if the ratio of the resultant comparison exceeds a preselected value, the attenuator plates are driven so as to intercept radiation which would be impinging on the detector having the higher X-ray intensity. Since the X-ray intensity level is highest in those areas outside the target area, the attenuators in essence track the edge of the target. Properly adjusted, the edges of the attenuator plates 120 intersect the target edge, i.e., the skin line, at the midpoint of the rectangular collimating slit 56 in the collimator 58. Reduction of the radiation in the areas outside the target improves the contrast for the target areas. As shown by FIGS. 5 and 6, the collimator blades 120 are both angled and tapered to shape the beam to the skin line of the patient. Tapering may be implemented in the form shown by stacking multiple plates of different dimensions so that a stepped taper is created at the target edge of the plate 120. FIG. 7A is an edge view of the collimator plates 120 illustrating a stacked arrangement to provide additional gradation of the X-ray fan beam intensity. The maximum blade thickness is selected to provide the desired raw beam film density by tapering each blade in two directions. This provides a filter which is thicker at the beginning of the scan where the exposure is likely to be high and thinner at the end of the scan where the exposure is likely to be low. This provides the desired film density at and outside the target skin line.

Figure 7B:
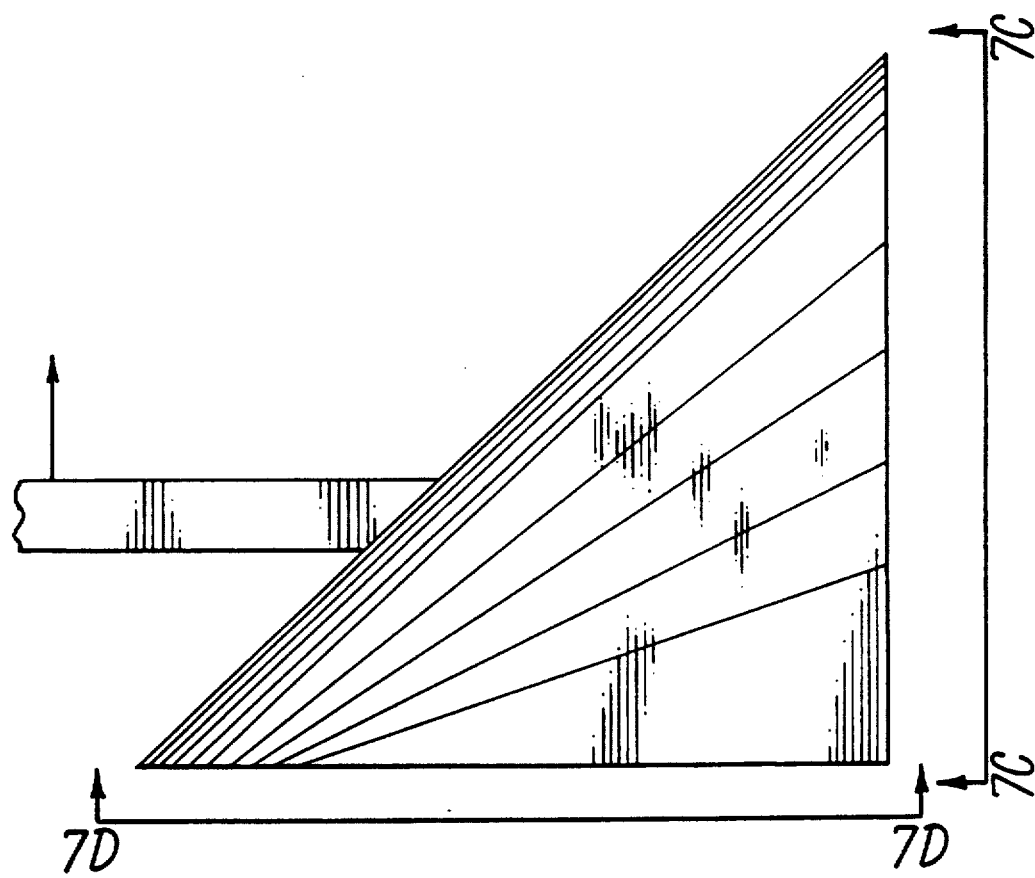
Figure 7C:
Figure 7D:
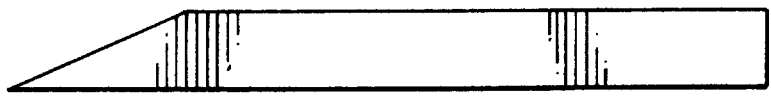

Note also that the collimator blade is angled with respect to the fan beam width or scan direction. This provides additional tapering of the X-ray intensity reaching the target, film and detector. FIGS. 7B, 7C, 7D are plan, right edge and front edge views of one collimator blade 120 showing the two-directional tapering of the blades.

An additional advantage obtained from the scanning X-ray beam of the present invention is that with the scanning occurring at a constant speed, the same exposure time occurs over all areas of the target. This constant exposure time eliminates increased dosage due to film reciprocity failures since the intensity control continuously maintains a constant X-ray intensity over all areas of the target to a predetermined value commensurate with a desired image contrast.

In addition to the features described above for obtaining a desired shaped beam and for scanning the beam across a target area, it has further been found that improved beam formation can be achieved by the addition of another collimator adjacent the X-ray window within the X-ray tube. In particular, with reference to FIGS. 8A and 8B, an off-focus X-ray beam, indicated by lines 130, is generated from the anode 68 of X-ray tube 50 and includes some amount of off-focus radiation. This off-focus radiation can adversely affect image quality. Elimination of the off-focus radiation contributes to the quality of images generated by the X-ray beam. Applicants have found that inserting a small apertured attenuator 132 into the X-ray beam adjacent an integral X-ray tube window 136 is effective in eliminating off-focus radiation. The attenuator 132 is positioned very close to the tube focal spot, e.g., about one inch, and provides a small aperture 138 through which radiation is allowed to pass. The X-ray tube window 136 is typically a beryllium material while the attenuator 132 is formed of an X-ray attenuating material such as lead. This could not be feasible in systems in which the entire target area must be illuminated simultaneously. The pivoting tube and small slit aperture associated with a fan beam scanning system also allow the use of an anode with a reduced target angle which improves tube loading.

B. AIR INTERSPERSED MOVING GRID

The invention thus far described provides an improved means for obtaining a mammography X-ray image through the use of a moving slit in which adjacent areas of a stationary X-ray film are sequentially exposed during a relatively short period of time. The system uses an array of X-ray dose sensors or detectors located behind the film and target area to continuously regulate both the X-ray tube kVp and the position of a pair of lateral collimator blades, both of which are used to provide optimum X-ray film exposure dose characteristics. One major advantage of this method of control is to minimize and possibly eliminate the need for often painful compression of the patient's breast to a rather flat, uniform thickness of breast tissue, which procedure has been necessary to provide relatively uniform X-ray density characteristics as required for best diagnosis when using conventional fixed X-ray exposure techniques during a mammography X-ray procedure. Another major advantage in the disclosed system is that there is a reduction of X-ray dosage to the patient necessary to produce an X-ray mammogram equivalent to an X-ray mammogram produced using more conventional X-ray apparatus. Another major advantage is the improvement in image quality through a reduction in scattered rays reaching the film.

The grid 62 described in regard to FIG. 3 eliminates or minimizes scatter or secondary X-rays. This is accomplished as a result of the narrow fan beam and X-ray opaque belt reducing scatter in the scanning direction without attenuating the primary X-rays while the air interspersed grid reduces scatter in a direction perpendicular to the scan direction without attenuating the primary X-rays. Due to the nature of such a grid, it is preferred that the grid be in motion during the exposure so that the septa (lines) of the grid are blurred across an area of the film rather than being seen as distinct lines. It has been known to provide grids of this type and such grids are typically referred to as Bucky grids. It will be appreciated that prior grids used in mammography applications were relatively large grids covering the entire target area inasmuch as the X-ray beam was designed to cover the entire target area in a single exposure. The septa or grid elements in these grids were spaced by plastic or other suitable material which could be embedded between the grid elements and provide structural support for the grid. A disadvantage of this type of grid structure is the X-ray absorption characteristics of the spacing material. Since the grid is positioned between the target and the film, the absorption characteristics affect the amount of radiation reaching the film but do not reduce the intensity of the radiation passing through the target area. Consequently, the patient may be exposed to higher than required X-ray dosages in order to obtain a desired film image.

One of the major advantages of the present invention is the ability to construct a grid in which the interstitial material between the grid elements is air. In this form, there is substantially no attenuation of the X-ray beam between the target area and the film cassette. This form of grid can be constructed with the present invention since the narrow dimension, i.e., approximately one inch, would be no wider than the aft slit of the system so that each of the septa having relatively short length. Accordingly, the septa can still be made extremely thin and maintain uniform spacing over the entire grid area without additional interstitial support.

While it has been known to provide a controlled reciprocating motion of a grid during X-ray exposure, such reciprocation has not been previously combined with scanning motion of the grid. One method for implementing a reciprocating motion of a grid is to provide a serpentine type slot, such as is shown at 140 in FIGS. 9A-9D, in a reciprocal cam bar 142. At least one end 144 of the grid 62 is provided with a roller 146 which fits snugly in slot 140 so that as the grid is driven in its scanning motion, the serpentine slot 140 forces the grid to move with a reciprocating motion. Beginning with FIG. 9A, the grid 62 and cam bar 142 are shown in a starting position. The grid must be started in its reciprocating motion prior to energizing the X-ray source in order to provide uniform exposure. Accordingly, the first step is to start the cam bar 142 in a forward motion as indicated by arrow 148 causing grid 62 to begin moving in the direction indicated by arrow 149. FIGS. 9B and 9C show how the cam bar motion has effected reciprocal motion of the grid 62 without any forward or scanning motion of the grid. Starting from the position shown in FIG. 9C, the cam bar 142 has stopped moving and the grid 62 is being driven in a scanning motion which causes the grid to continue to move reciprocally as the roller 146 follows the track 140. The X-ray source may be energized as the grid reaches the position of FIG. 9C and begins its scanning motion. The cam bar 142 may remain at the position of FIG. 9D until the end of scan at which point both the cam bar and grid are returned to the position shown in FIG. 9A.

The above described mechanism provides the advantage of a carefully defined and regulated grid motion as a function of scan motion combined with essentially instant reversal of the grid motion necessary to minimize grid line artifacts in the X-ray mammogram. However, the grid motion is achieved by purely mechanical means and is subject to wear and potential jamming as the grid motion is reversed within the serpentine slot.

Figure 10:
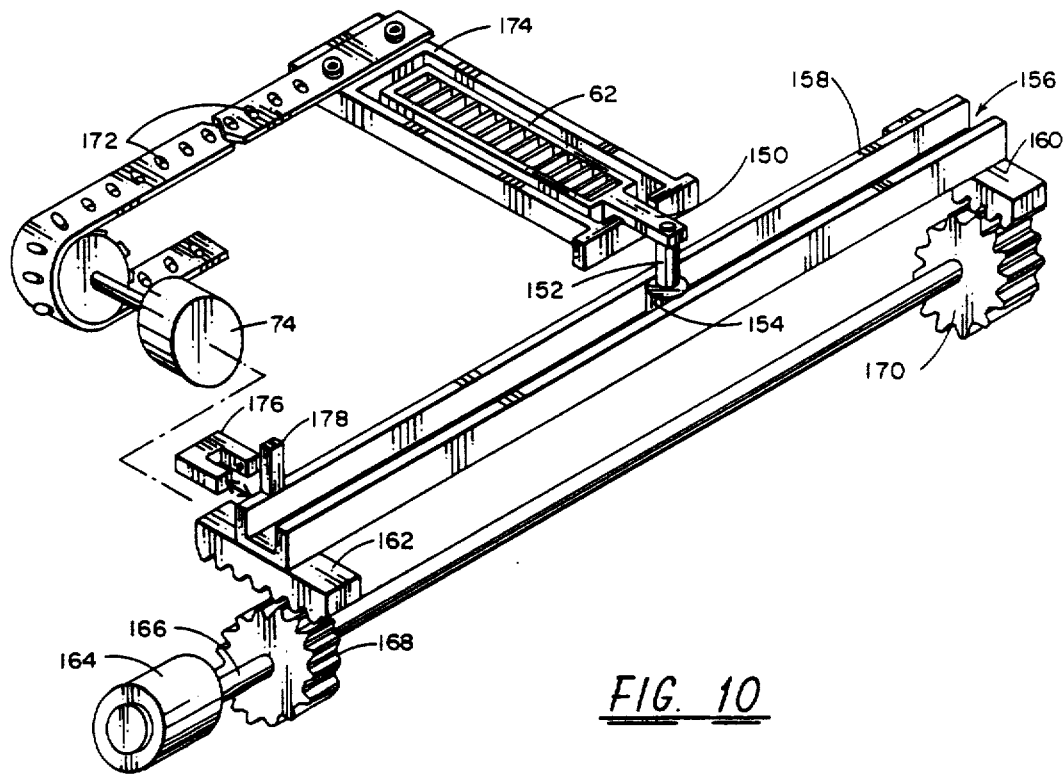
FIG. 10 illustrates a preferred method of obtaining scanning and reciprocating motion of an X-ray grid.

FIG. 10 illustrates a preferred form a grid drive mechanism utilizing electric drive motors for providing both the forward or scanning motion of the grid 62 and the reciprocating or Bucky motion of the grid. In this embodiment, the grid 62 includes an extending arm 150 to which is attached a depending member 152 terminating in a roller 154. The roller 154 glides in a slot 156 in a bar member 158. Each end of the bar member 158 is attached to a corresponding geared rack 160, 162. A reversing drive motor 164 drives a shaft 166 coupled to first and second pinion gears 168 and 170. Each of the pinion gears 168, 170 engage corresponding ones of the racks 162 and 160. As the motor 164 is driven in a reciprocating fashion, the member 158 connected to the racks 160 and 162 is similarly driven in a reciprocating motion causing the grid 62 to also move reciprocally. The scan drive motor 74 drives a belt 172 which causes the grid 62 to be moved in its scanning motion. The grid 62 is supported in a holder 174 which permits the reciprocating motion of the grid 62 while allowing it to be driven in the scanning direction. The motor 164 can be coupled to the motor control 86 of FIG. 3 and be driven in the control fashion as motor 74.

It will be appreciated that a finite time is required for the grid to reverse direction of reciprocation even in the electronically embodied invention of FIG. 10. Furthermore, to be effective in eliminating grid lines, the reciprocating motion of the grid must maintain a uniform velocity. Since this uniform velocity requirement is not consistent with the need to reverse the grid travel direction, an additional system modification has been implemented in order to eliminate grid lines resulting from grid velocity changes. In particular, the X-ray beam exposure is modulated in synchronization with the grid reversal. For example, if grid reversal occurs once each time the fan beam travels on slit width and if exposure is turned off during a reversal, then reversal grid lines would be eliminated. Typically, grid reversal occupies less than ten percent of the fan beam exposure. Thus, the exposure reduction would be less than ten percent. However, it has been found that reducing the X-ray intensity by fifty percent sufficiently reduces the grid lines to that the total overall exposure reduction is less than five percent. The exposure reduction may be synchronized with scanning of the fan beam through use of a chopper wheel or more preferably by modulating the kVp to the X-ray tube. Such a method and apparatus is disclosed in U.S. patent application Ser. No. 361,989, filed June 5, 1989, and assigned to General Electric Company, the disclosure of which is hereby incorporated by reference.

One method of synchronizing or modulating X-ray energy in conjunction with reversals of the grid motion is to incorporate limit switches, one of which is illustrated at 176, adjacent the rack 162 so that one of the switches is actuated at each extreme end of travel of rack 162. The signals produced by actuation of the limit switches such as by contact with rack 162 can be coupled to processor 36 (FIG. 2) to effect a reduction in kVp at turn-around. While limit switches are an acceptable method of detecting turn-around position, they do require mechanical adjustment from repeated contact. An alternate method which obviates mechanical contact is to provide infrared limit switches of a type well known in the art. The switch 176 is illustrated as an infrared limit switch. Such switches commonly employ a C-shaped holder with an IR beam passing through the gap between opposed arms of the C-shaped holder. Interruption of this beam by an object entering the gap, produces a detectable signal. The holder could be arranged to receive an end of the rack 162 in the gap or an extension could be attached to the rack 162 for intercepting the IR beam.

An alternative to the reciprocating motion of the grid is to design the grid such that the individual elements are tilted or angled so that all points on the film cassette would experience the same duration of septal shadow transit and interstitial exposure. Referring now to FIGS. 11A-11D, there is shown at FIG. 11A an arrangement of septa 180 for positioning in a grid. FIG. 11B shows the result of scanning over an X-ray sensitive film 182 with an X-ray beam 184 while moving the septa only along the direction of scanning, i.e., the septa 180 are not moved reciprocally as was described with regard to FIG. 10. A plurality of septal shadows 186 would be found on the film 182 below the grid. If the individual septa 180 are tilted at an angle to the direction of travel as shown in FIG. 11C, each portion of the film 182 will be exposed to the same amount of septal shadow so that the resultant film, while having lower contrast, will not have individual shadows visible. FIG. 11D illustrates the result of scanning with tilted septa. Note that the condition for scanning such that each point on the film experiences the same direction of septal shadow transit and interstitial exposure is to place the septa at an angle a equal to arctan S/D as shown in FIG. 11D, where S is the horizontal distance between septa and D is the width of the X-ray beam. This arrangement could be extended to the condition of having the septa at an angle of arctan (N*S/D) so that each point experiences N septal shadows during beam transit. As N is increased, the potential for interseptal artifacts that would occur along the dotted lines in FIG. 11D would be reduced. However, for dimensionally long scans, the focal spot becomes misaligned with the grid focal line with consequent reduction in grid efficiency in reducing scatter. The serpentine cam (FIG. 9) would now be angled for only the first grid oscillation.

Figure 13:
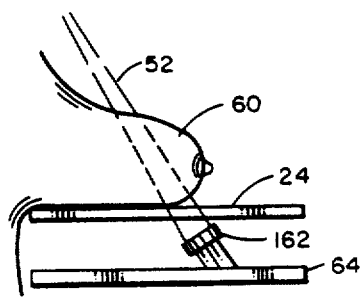
FIG. 13 is an exaggerated representation of the effect of tilting of a grid.
Figure 12:
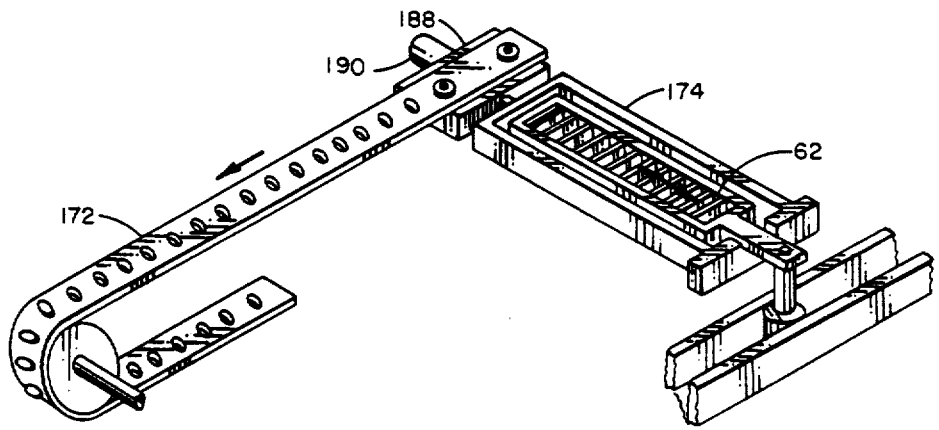
FIG. 12 illustrates an arrangement for tilting of grid to reduce attenuation at scan extremes.

It will be appreciate that with a scanning beam arrangement, if the scan is over a relatively large dimension and the grid is thick, i.e., high grid ratio, the angle of incidence of the scanning beam into the relatively narrow grid will result in some attenuation of the X-ray beam at extremes of the scan. For relatively short scans of the type contemplated in this invention, it is not anticipated that attenuation at scan extremes is significant. Also, the fan beam can be slightly narrower than the grid width. However, one solution to overcoming the problem of attenuation at scan extremes is to make the grid slightly wider than the scanning X-ray beam and to rotate the grid as it is moved across the target area so that it is maintained in a plane substantially perpendicular to the X-ray beam. FIG. 12 illustrates one embodiment of this invention. The movement would be controlled by a gear box 188 on one side of the grid 62 with the gear box being driven through a drive motor 190 attached to the side of the gear box 188. This rotation would assure that the grid was always in focus with the image plane and the focal spot. The grid 62 would be essentially the same as is shown in FIG. 10 but the grid holder 174 would be modified to be tilted or angled by the gear box 188. Note that in this embodiment, the gear box 188 would be fixed to the belt 172 so that its driving function with regard to the holder 174 would be such as to cause the holder to gradually tilt or change its angle as it travels from the extreme ends of the scanning beam direction. FIG. 13 is a schematic representation, greatly exaggerated, of the effect of tilting of the grid 62.

C. SCATTERED X-RAY ATTENUATION

In order to improve X-ray image quality and contrast in particular, it is important to provide collimation of the primary X-ray beam to the smallest possible area, not only at the entrance to the X-ray film cassette but also to provide matching collimation between the patient and the X-ray source or tube. Such collimation and matching serves to minimize scatter radiation originating from tissue not being imaged by the primary X-ray beam. Such scatter radiation can strike and cause fogging on the X-ray film otherwise being exposed by the primary beam. In the present invention, the X-ray beam is scanned across a target and both a collimator 58, a collimator 120 and a grid 62 are used to minimize the presence of scatter radiation received by the X-ray film. However, X-rays which strike and are deflected by collisions within the target 60 may be deflected outside of the grid area and cause fogging of the film. The present invention addresses X-rays outside of the grid area by providing an attenuator bounding the grid 62. One of the characteristics required of such an attenuator is that it take up essentially no space when the grid is positioned at an edge of the film table 24. That is, when the grid is positioned adjacent or abutting a patient's chest wall during a mammography procedure, the attenuation means must take up essentially no space so that a full image of the patient adjacent the chest wall may be obtained. Similarly, at the opposite end of the travel of the scanning beam, it is desirable that the attenuation means not interfere with the full scan dimension.

Figure 14:
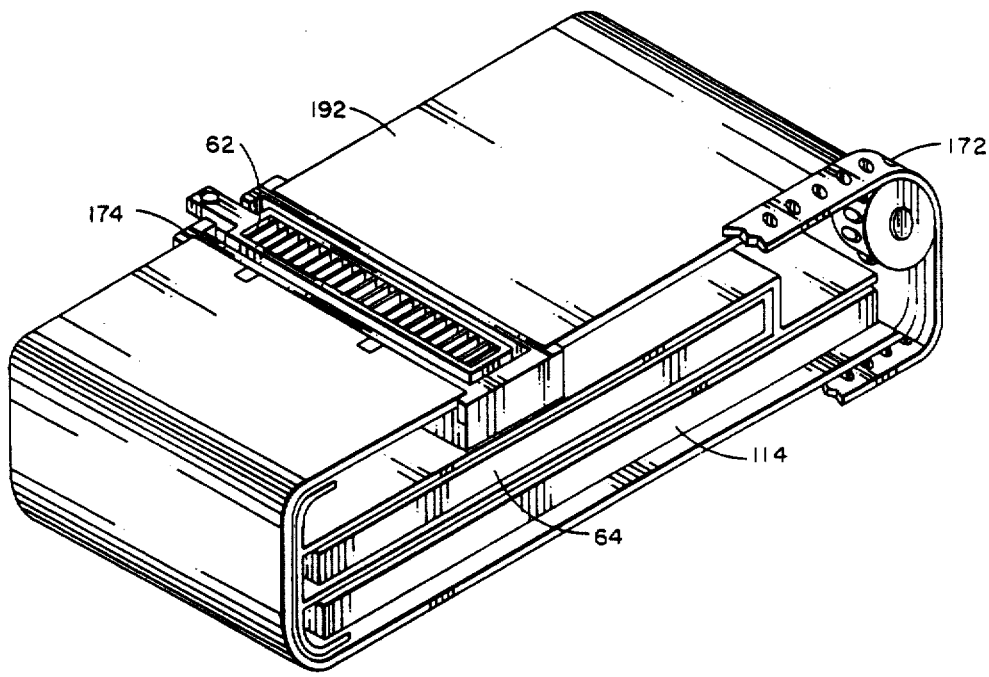
FIG. 14 is a perspective view of a film table assembly, less casing, showing the arrangement of an X-ray impervious belt for blocking scatter radiation.

In accordance with the present invention, the attenuation means is constructed as a wide flexible belt which may comprise a thin rubber or plastic membrane uniformly embedded with lead or lead oxide particles for X-ray attenuation. Referring now to FIG. 14, there is shown one embodiment of the film table 24 incorporating the grid assembly and a lead shutter belt 192 in accordance with the present invention. For clarity, the outer casing of the table 24 has not been shown but such casing is essentially the same as found on machines such as that shown in FIG. 1. The belt 192 is preferably reinforced by using a woven synthetic fabric which is further reinforced against tearing or stretching through the use of a thin sheet of Mylar plastic. The Mylar plastic reinforcement material may be applied to the leaded belt by means of a pressure sensitive adhesive coating. As described above, the aft slit or grid 62 is motor driven through its motion using a flexible cog type drive tape system with a corresponding pulley on a gear drive motor as shown in FIG. 10. Referring to FIG. 14, opposite ends of the lead attenuating belt 192 are secured to the leading and trailing edges of the grid frame 174 so that the belt moves concurrently with the assembly. The belt is continuous and recirculates under the film cassette area and the detector array assembly. Any X-ray radiation scattered by the target so that it falls outside the grid 62 will intersect and be essentially absorbed by the belt 192. Thus, the belt 192 provides an effective attenuator of scatter radiation.

D. VARIABLE FILER MAMMOGRAPHY

It is known that there exists an optimum kVp and filter for maximizing contrasts while minimizing patient dose during mammography procedures. For a small to medium size patient, good results are often obtained at X-ray voltages in the range of twenty-eight to thirty-two kVp with a molydenum target and molydenum filter X-ray tube. This arrangement is, however, not appropriate when higher tube voltages are used to penetrate the more dense patient. For voltages in the range of thirty to forty kVp, it is desirable to replace the molydenum filter with a filter of higher atomic number. A filter formed of silver is sometimes used since it filters the hard radiation which reduces contrasts while transmitting radiation in the twenty to twenty-five key energy range. In conventional mammography, a single selection of kVp filter is required. The exposure is thus optimized for only one patient transmission value. In the present invention of equalized slit scanned mammography, patient transmission is detected continuously during the scan and selection of an appropriate filter is possible.

Referring again to FIG. 3, there is shown a filter 194 positioned below the X-ray tube for filtering X-rays produced by the tube 50. In the present invention, the output signals from the detector 114 used to set the kVp of the tube are also provided to control the filter 194 to vary its position as a function of the tube kVp. The filter may be motor driven using a rack and pinion arrangement as has hereinbefore been described or may merely be two alternative filters which are selected depending upon whether the kVp is above or below a specific set point. A continuous filter could be constructed of different materials which could be varied by rotating various sections of a disc into the X-ray beam 52. More particularly, a rotatable disc could be constructed having arcuate sections formed of different materials having different predetermined X-ray attenuation characteristics. The disc could be placed in a position in the X-ray beam such that the disc could be selectively rotated to place a selected one of the arcuate sections into the beam for selectively attenuating the beam. The use of a disc or wheel of this type is well known in other fields such as, for example, television in which color wheels having long been known.

E. CONTROL SYSTEM

Figure 15:
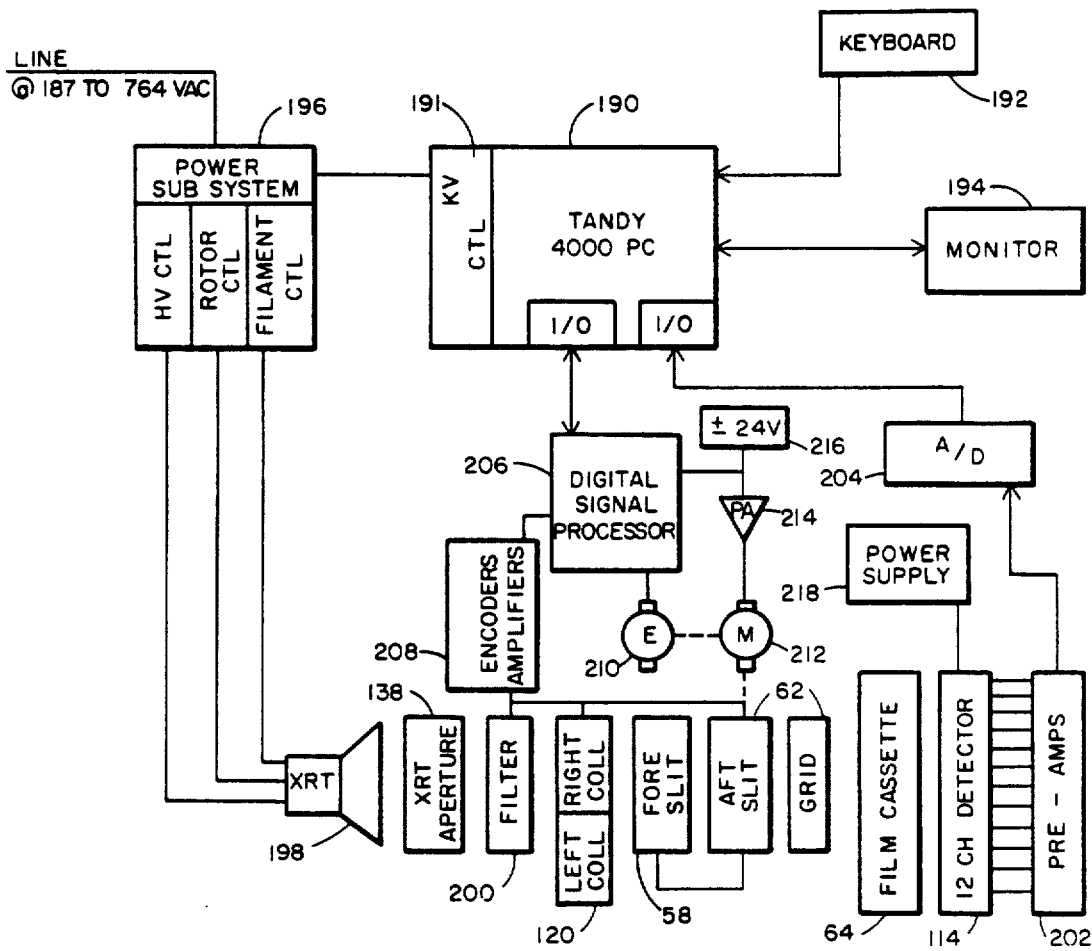
FIG. 15 is a functional block diagram of a system for controlling a mammography machine in accordance with the present invention.

The general control system for a prior art mammography machine was described above with regard to FIG. 2. The control system, more specific to the present invention, will be described hereinafter with regard to FIGS. 15–18. Turning first to FIG. 15, there is shown a general control system in a functional block diagram form which may be used with the present invention. The system may be implemented around a general purpose computer such as a Tandy 4000 personal computer indicated generally at 190. Associated with the computer 190 is a keyboard 192 and a monitor 194. These three elements together form a general personal computer system of a type well known. The computer 190 may include an analog voltage control circuit which converts the digital signals used by the computer into appropriate analog control signals for controlling the X-ray power unit 196 supplying power to the X-ray tube 198. Both the power unit 196 and the X-ray tube 198 are commercially available devices commonly employed in presently available mammography machines. Positioned in front of the X-ray tube 198 is an X-ray tube aperture previously identified as aperture 138 in disc 132 of FIG. 8. Proceeding from the X-ray tube through the aperture and down to the multi-channel detector 114, the next element following the aperture is the above mentioned filter indicated at 200 which can be adjusted to change the average X-ray energy. Below the filter 200 are the left and right collimators 120 described with regard to FIG. 5. Next in line is the four slit or fan beam collimator 58. Below the collimator 58 is the combined aft slit and grid 62 described in detail in FIG. 10. A film cassette 64 containing X-ray film is positioned below the grid 62. The detector 114, which comprises a plurality of spaced X-ray sensors is positioned beneath the film cassette 64 with each of the sensors being connected through corresponding preamplifiers 202 to provide output signals indicative of the intensity of X-ray radiation impinging on the detector. The signals from the preamplifiers 202 are coupled to an analog to digital (A/D) converter 204 and from the A/D converter to an IO port of the computer 190.

The computer 190 also provides drive signals to a digital signal processor 206 which converts the digital signals to appropriate drive signals for controlling the motors coupled to the collimators 120, the filter 200, and the aft slit and grid 62. The processor 206 also receives information from the motor encoders indicative of the position of the motors and converts those signals to appropriate digital signals for application to an IO port of the computer 190. The motor encoders and amplifiers are indicated in block diagram form at 208. Each of the motor encoders comprises an encoder such as is illustrated at 210 coupled to a motor such as illustrated at 212. The motor 212 is driven through a power amplifier 214 from the processor 206. A power supply 216 delivers plus and minus 24 volt power to the power amplifiers and other processing units in the system. A separate power supply 118 is provided for the multi-channel detector 114.

Figure 16:
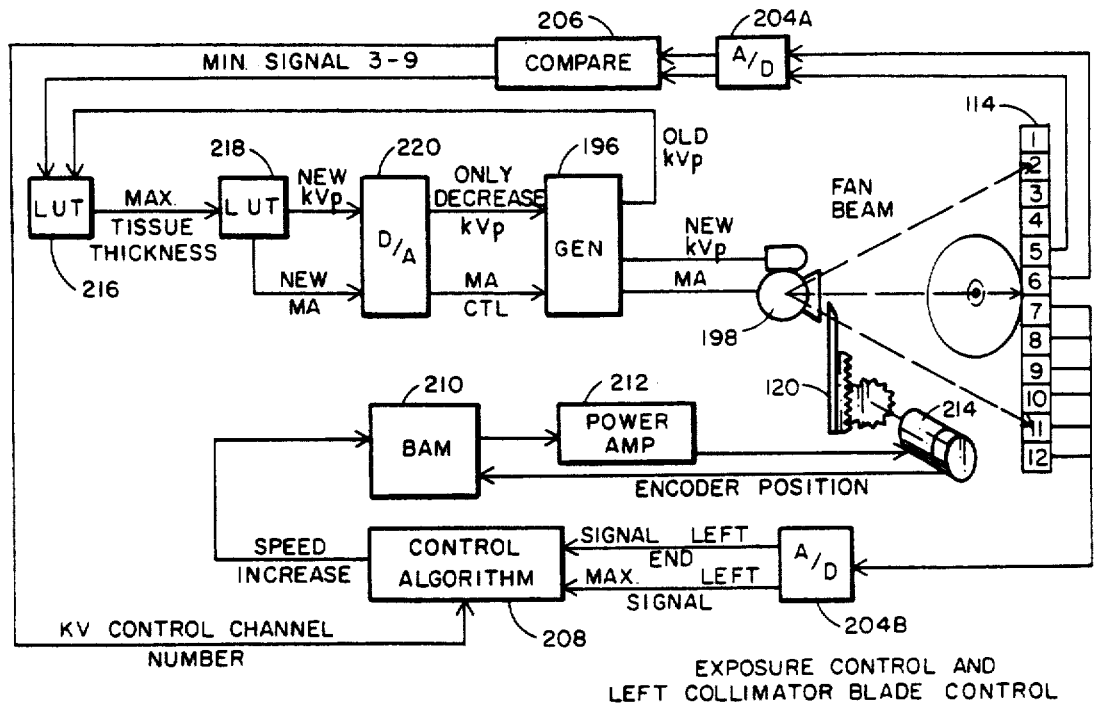
FIG. 16 is a functional block diagram of an exposure and collimator control system in accordance with one aspect of the present invention.

FIG. 16 is a more detailed functional block diagram of an exposure control and left collimator blade control for use in the system of FIG. 14. For controlling the left collimator blade 120, the A/D converter 204 can be functionally considered to be two separate A/D converters 204A and 204B. The detector 114 is divided into a left half and a right half. The sensor elements labeled &-12 are considered to be on the left half of the detector while sensor elements 1-6 are on the right half. The actual dividing point is determined automatically as the minimum signal or kVp control signal element. Each of the sensors 7-12 provide signals which are coupled to A/D converter 204B. The reference signal would normally be detector channel 12 which receives radiation that has passed through the full thickness of the collimator blade. The converter 204B selects from those signals a left end signal and a maximum left signal. The converter 204A receives signals from a predetermined number of sensors selected to at least cover the most dense areas of the target. For example, signals from sensors 3-9 may be sampled so that converter 204A provides an output signal indicating the sensor producing the minimum amplitude signal. That sensor will be associated with the thickest part of the target area since that part of the target area will provide maximum attenuation. For providing this comparison, there is provided a comparison circuit 206. The signal from the comparison circuit 206 indicates which of the sensors is producing the minimum signal. This information is passed to the computer 190 and is processed in a control algorithm indicated by block 208. For the left collimator blade, the control algorithm multiplies the intensity of the signal in the maximum left channel by a predetermined number such as, for example, 1.2, and then determines if the maximum left signal product is greater than the reference signal. If the maximum left signal product is greater than the reference signal, then the left collimator blade is moved in at a greater rate than its normal programmed rate. It will be appreciated that the control algorithm anticipates a constant speed of closing of the left collimator and therefore the calculation is only to determine whether or not to increase the speed. The signal from the control algorithm block 208 is supplied to a motor control block 210 which then furnishes a signal to a power amplifier 212 for driving the motor 214. The motor 214 is coupled by a rack and pinion gear arrangement to the left collimator 120. Position of the motor, and therefore the position of the collimator 120, is provided by encoder feedback signal to the motor control 210.

Exposure control is obtained by supplying the signal from the comparator 206 to a look-up table 216 which provides an output signal representing maximum tissue thickness to a second look-up table 218. The look-up table 218 contains data which converts the maximum tissue thickness information to kVp and Ma data for supplying to a D/A converter 220. The D/A converter 220 converts the digital information to signals for the power generator 196. The power generator 196, in turn, provides appropriate power to the X-ray tube 198. The feedback signal from the X-ray tube indicating the last kVp value is provided both to the generator 196 for closed loop control and also to the look-up table 216 for coordination with the minimum signal information supplied from the comparator 206. Control of the right collimator is essentially the same as the control of the left collimator.

Figure 17:
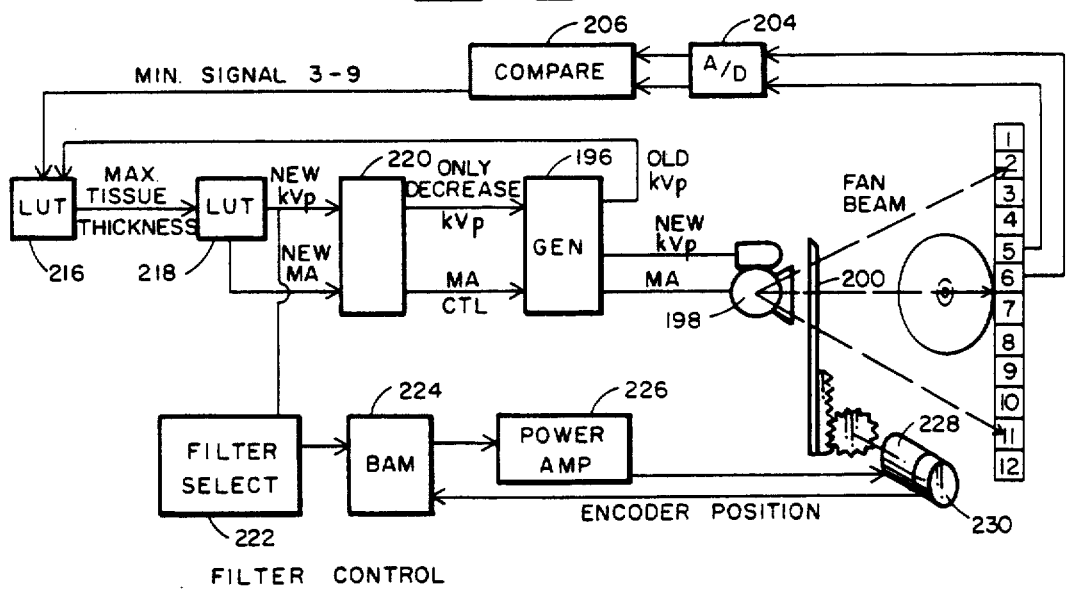
FIG. 17 is a functional block diagram of a method for controlling a filter in accordance with one aspect of the present invention.

FIG. 17 illustrates one method of control of the filter 200 positioned in the X-ray fan beam. In this figure, the new kVp information provided from the look-up table 218 is applied to a filter select circuit 222. The filter select circuit determines from the kVp value a particular type of filter or attenuation level to be placed in the X-ray beam. This information is supplied to a motor control 224 which in turn provides drive signals through a power amplifier 226 to a motor 228 driving the filter 200. As with the prior art driving mechanisms, the motor 228 may drive the filter through a rack and pinion gear arrangement of a type well known in the art. Closed loop control is effected by an encoder 230 coupled to the back of the motor 228 which provides feedback signals to the motor controller 224.

Figure 18A:
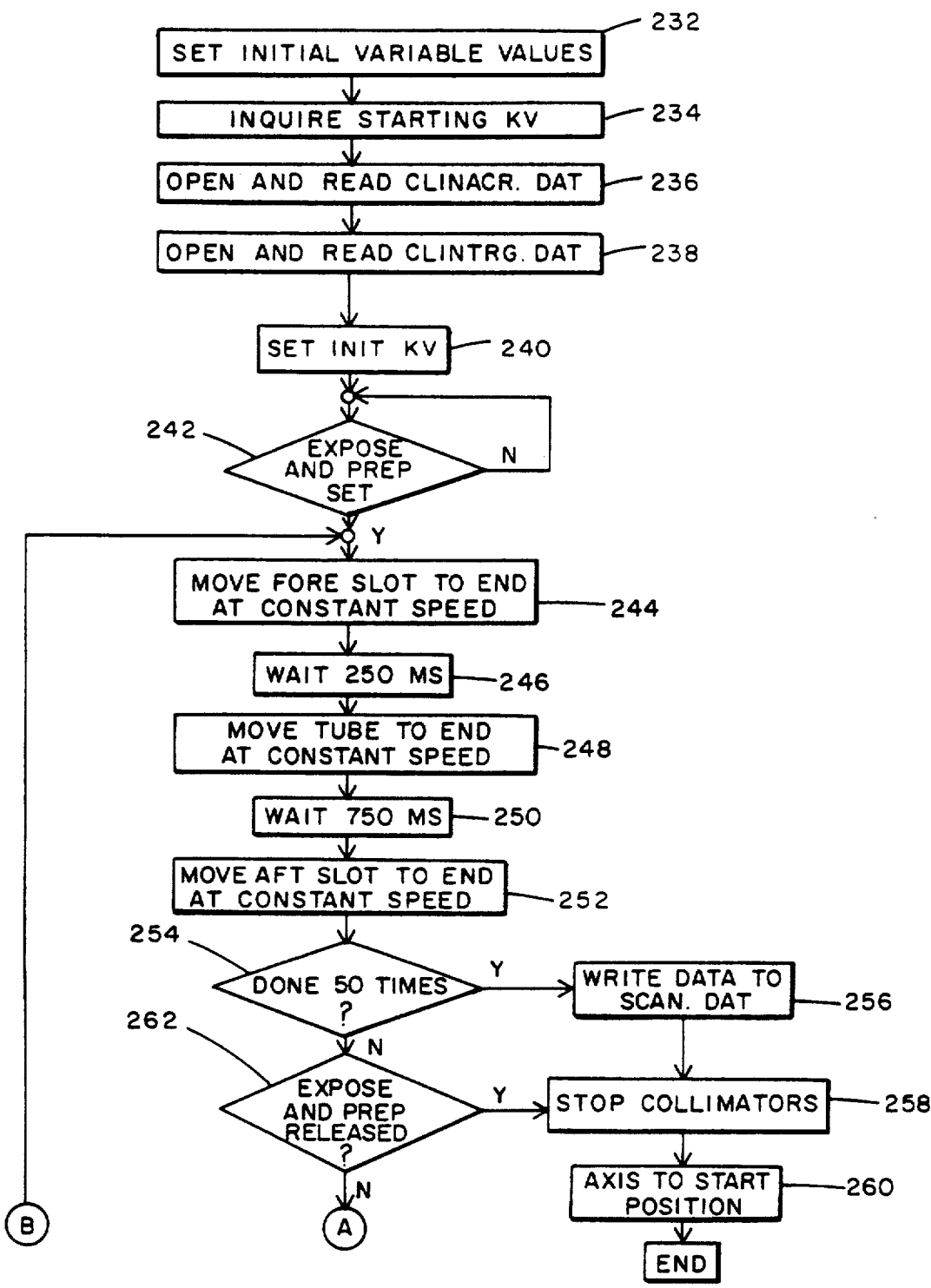
FIGS. 18A and 18B are a flow chart of a program for scanning the fan beam, kVp and Ma and adjusting collimator blades to attain a desired image contrast in one form of the present invention.
Figure 18B:
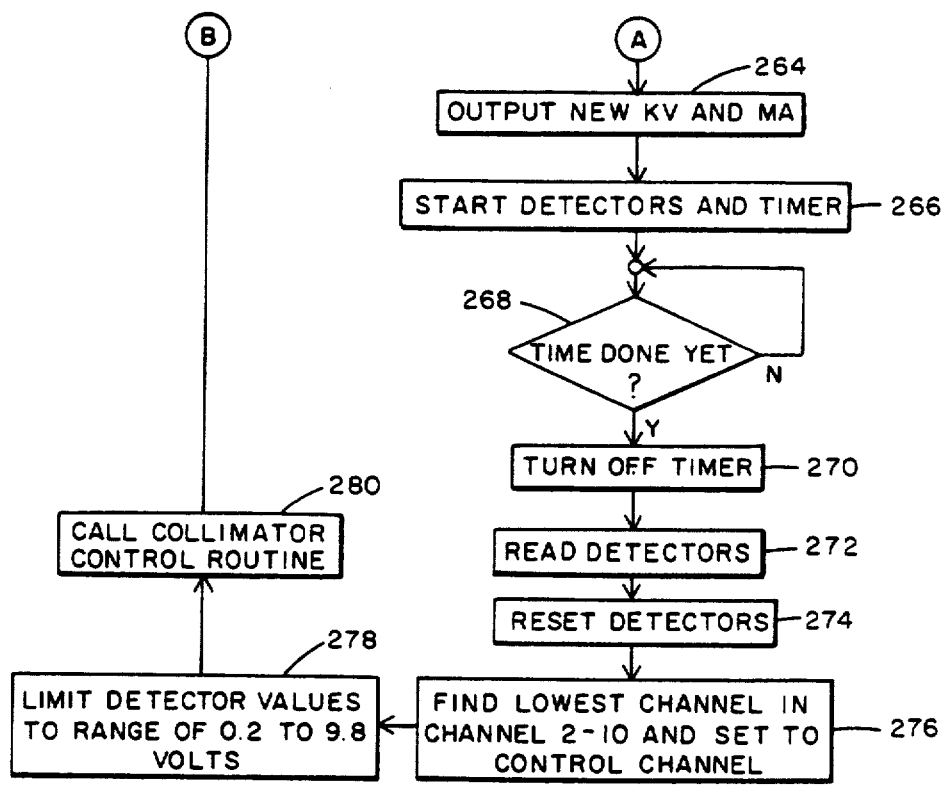

Referring now to FIGS. 18A-18B, there is shown a flow chart of a control routine for controlling the kVp and Ma output of the generator 196. Initially, certain variables are set based on prior experience of the X-ray operator as indicated by the block 232. The starting kVp, which has been selected in the block 232, is recognized by the equipment as shown in block 234 and the processor then determined the patient thickness given the starting kVp and the minimum detector signal s is illustrated by the look-up table 216. This is shown in block 236. Once the patient thickness has been determined, the algorithm next determines the appropriate kVp for the generator from a second look-up table indicated as 218 in FIG. 16 and as shown by block 238. Once the initial kVp has been set, as indicated by block 240, the processor tests to determine whether or not the operator has indicated an exposure to start as is indicated by block 242. The processor will loop at this block until an exposure command is received. Once the exposure command is received, the fore slot or collimator 58 is driven to its start position as indicated by block 244. After 250 milliseconds, the X-ray tube 198 is then moved to its start position as indicated by blocks 246 and 248. After 750 milliseconds, the aft slot or grid is moved to its start position as indicated by blocks 250 and 252. While each of these elements may already be in the initial position, this portion of the algorithm is required in order to assure that each element is properly positioned prior to start of a scan. Once each element is in position, the exposure begins and the program determines the number. If more than fifty have been performed, data is written out to a printer as indicated at blocks 254 and 256. Immediately after writing, the program stops the collimators and returns all axes to their start position before ending the routine as indicated at blocks 258 and 260. If the routine has not been processed the predetermined number of times, the program steps to the block 262 to determine whether or not the operator exposure button has been released. If the exposure button has been released, the program steps to the block 258. Otherwise, the program continues to compute the proper kVp and Ma as was described with regard to FIG. 16, and as shown by block 264. Each of the signals from the detectors is integrated for approximately two-tenths of a second and then reset to continue to collect the data as indicated at block 266. The control algorithm includes a loop indicated by block 268 for determining whether or not the integration time is over. At the end of the integration time, the fractional second timer is turned off as indicated by block 270, the detectors are read as indicated by block 272, and the detectors are rest as indicated by block 274. The program then determines the lowest signal in the detector channels such as in channels 2-10 or 3-9 and sets that channel or sensor to be the control sensor as indicated by block 276. The signal from the detectors is limited to a predetermined range which may be, for example, from 0.2 to 9.8 volts as indicated by block 278. Once the detector values have been determined, the collimator control routine, as was described with regard to FIG. 16, is implemented in order to control the position of the collimators. The process is then continued by returning to block 254 to determine whether or not it has been through fifty iterations.

Figure 19:
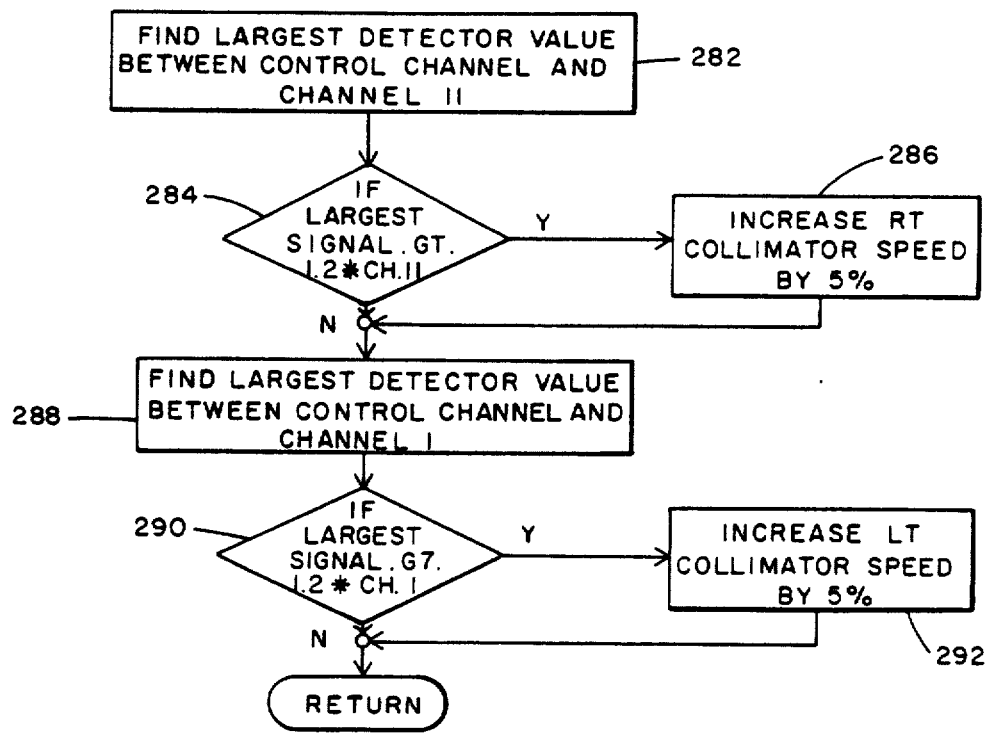
FIG. 19 is a flow chart of one form of collimator control routine for use with the flow chart of FIGS. 18A-18B.

The collimator control routine is shown in FIG. 19 beginning with block 282 in which the largest detector value between the control channel and the end channel is identified. The routine then determines if the largest signal is greater than 1.2× an outer channel, e.g., channel 11, block 284 and if it is, then increases the collimator speed by five percent, block 286. If it is less than 1.2, the program steps to determine the largest detector value between the control channel and channel 1, block 288. Note that this process first operates on the right collimator and then subsequently on the left collimator. Following the same routine, if the largest signal on the left side is greater than 1.2× the first channel or channel 1, block 290, then the left collimator's speed is increased by five percent, block 292. The program then exits until it is next called by the routine shown in FIGS. 18A, 18B.

While only certain preferred features of the invention have been shown by way of illustration, many modifications and changes will occur to those skilled in the art. It is, therefore, to be understood that the present claims are intended to cover all such modifications and changes which fall within the true spirit and scope of the invention.

What is claimed is:

1. A method of improving imaging in an X-ray mammography machine having a controllable X-ray source for generating an X-ray beam of selected radiation intensity and a target area for the X-ray beam, the method comprising the steps of:
   directing the X-ray beam in a preselected configuration onto a part of the target area;
   detecting the radiation intensity of the X-ray beam in each of a plurality of substantially equal segments of the target area;
   identifying at least one segment of lowest radiation intensity;
   adjusting the X-ray source to establish a predetermined radiation intensity in the identified at least one segment;
   identifying other segments each having a radiation intensity greater than a predetermined percentage of the predetermined radiation intensity in the identified at least one segment; and
   attenuating the radiation intensity directed toward the identified other segments.

2. The method of claim 1 further comprising the additional step of translating the X-ray beam in the preselected configuration thereof over the target area.

3. The method of claim 2 wherein the translating step includes scanning at a constant speed to produce a fixed exposure time for all areas of the target.

4. The method of claim 2 further comprising the further additional step of repeating from the detecting step through the attenuating step inclusive while continuing the translating step.

5. The method of claim 1 wherein the X-ray mammography machine also has a collimator and wherein the directing step includes positioning the collimator adjacent the X-ray source in a position for blocking off-focus radiation.

6. The method of claim 1 wherein the X-ray mammography machine also has a collimator and wherein the directing step includes positioning the collimator in the X-ray beam such that the collimator shapes the beam into a fan shape.

7. The method of claim 1 wherein the X-ray mammography machine also has a detector including a plurality of strip-like elements and wherein the detecting step includes positioning the detector in a location for receiving X-ray radiation from the X-ray source after passage through the target area and sensing a signal from each element of the detector indicative of the X-ray beam energy impinging on each of the elements.

8. The method of claim 7 wherein the first identifying step includes selecting a lowest magnitude signal from the signals sensed during the sensing step for controlling the X-ray radiation intensity.

9. The method of claim 1 wherein the X-ray mammography machine further has a variable filter and wherein the adjusting step includes positioning the variable filter in the X-ray beam for establishing a minimum X-ray intensity in the target area.

10. The method of claim 9 wherein the translating step includes moving the grid at a generally constant speed to provide a generally uniform exposure time over the target area.

11. The method of claim 1 wherein the adjusting step includes selecting a kVp value corresponding to the predetermined radiation intensity level established during the adjusting step for energizing the X-ray source and setting an Ma value for the X-ray source corresponding to the selected kVp value.

12. A mammography machine comprising:
   a controllable X-ray source for generating an X-ray beam of preselected X-ray radiation intensity;
   first collimating means positioned in a path of said X-ray beam for collimating said beam into a fan shape:
   means coupled to said X-ray source for effecting movement of said source for causing said fan-shaped beam to scan across a target area;
   detection means positioned for receiving said X-ray radiation passing through the target area and for producing signals indicative of the intensity of said radiation, said detection means comprising a plurality of uniformly spaced detector elements, each element extending in a direction corresponding to the direction of movement of said beam, each of the signals representing radiation intensity at a corresponding one of said elements; and
   means responsive to a one of said signals from said detection means indicative of a minimum radiation intensity for controlling said X-ray source to establish a constant X-ray radiation intensity passing through the target area at each position of said scanning fan shaped X-ray beam.

13. The mammography machine of claim 12 and including a second collimating means positioned adjacent said X-ray source, said second collimating means comprising a substantially X-ray opaque member having a relatively small aperture formed therethrough, said X-ray beam being directed through said aperture such that off-focus radiation is attenuated by said substantially X-ray opaque member.

14. The mammography machine of claim 12 wherein said first collimating means includes a substantially X-ray opaque member having a rectangular slit formed therethrough, said opaque member being positioned in a path of said X-ray beam so as to form said beam into a fan shape.

15. The mammography machine of claim 12 and including a rectangular shaped air interspaced grid comprising a plurality of thin, plate-like members, each of the members being aligned on a corresponding radius of a circle centered on said X-ray source, said numbers being spaced one from another with only air in the spaces between said members, said grid conforming substantially to the shape of said fan shaped beam adjacent said target area.

16. The mammography machine of claim 15 and including means for reciprocatively moving said grid in a direction perpendicular to the direction of scanning of the X-ray beam, said moving means including means for effecting an interruption of said X-ray beam at each extreme position of reciprocal motion of said grid for a time sufficient to allow said grid to change its direction of motion.

17. A method for generating a collimate scanning X-ray beam over a predetermined target area from an X-ray source having a selected axis in an X-ray system having at least one collimator associated with the X-ray beam, the method comprising the steps of:
 rotating the X-ray source to a predetermined angular orientation with respect to the predetermined target area;
 energizing the X-ray source to cause the X-ray beam to illuminate a portion of the predetermined target area;
 initiating pivotable motion of the X-ray source generally about the selected axis at least substantially simultaneously with the occurrence of the energizing step;
 passing the X-ray beam through the at least one collimator to shape the X-ray beam into a predetermined configuration at the predetermined target area;
 moving the at least one collimator at least generally concurrently with the pivotable motion of the X-ray source such that the illuminated portion of the predetermined target area maintains a constant dimension;
 detecting the radiation intensity of the X-ray beam in each of a plurality of substantially equal segments of the predetermined target area;
 identifying at least one segment of lowest radiation intensity;
 adjusting the X-ray source to establish a predetermined radiation intensity in the at least one segment;
 identifying other segments each having a radiation intensity greater than a predetermined percentage of the predetermined radiation intensity established in the at least one segment;
 attenuating the radiation intensity directed toward the other segments; and
 terminating energization of the X-ray source when the predetermined target area has been illuminated by the X-ray beam.

18. The method of claim 17 wherein the X-ray system includes an electric motor coupled with the X-ray source and wherein the rotating step includes energizing the electric motor in one direction to cause the X-ray source to rotate to the predetermined angular orientation.

19. The method of claim 2 wherein the X-ray mammography machine also has a grid including a plurality of air interspaced elements each comprising a generally thin plate-like member aligned on a corresponding radius of a circle centered at the X-ray source and wherein the directing step includes passing the X-ray beam through the grid elements and reducing scatter radiation of the X-ray beam in response to the passing step, the passing step further including reciprocating the grip in a direction at least generally perpendicular to the direction of the movement of the X-ray beam during the moving step and interrupting the X-ray beam at each extreme position of the reciprocal motion of the grid for a time sufficient to allow the grid to change its direction of movement.

20. The method of claim 18 wherein the initiating step includes reversing the energization of the electric motor to effect the rotation of the X-ray source about the selected axis at least generally at a constant speed.

* * * * *